United States Patent
Lee et al.

(10) Patent No.: US 7,112,672 B2
(45) Date of Patent: Sep. 26, 2006

(54) PROCESS FOR THE SELECTIVE PREPARATION OF 3-(Z) PROPENYL-CEPHEM COMPOUND

(75) Inventors: Gwan-Sun Lee, Seoul (KR); Young-Kil Chang, Seoul (KR); Hong-Sun Kim, Seoul (KR); Jae-Heon Lee, Yongin-si (KR); Chul-Hyun Park, Seongnam-si (KR); Gha-Seung Park, Goyang-si (KR); Cheol-Kyung Kim, Namyangju-si (KR)

(73) Assignee: Hanmi Pharm. Co., Ltd., (KR)

( * ) Notice: Subject to any disclaimer, the term of this patent is extended or adjusted under 35 U.S.C. 154(b) by 233 days.

(21) Appl. No.: 10/475,057

(22) PCT Filed: Apr. 17, 2002

(86) PCT No.: PCT/KR02/00700

§ 371 (c)(1),
(2), (4) Date: Oct. 16, 2003

(87) PCT Pub. No.: WO02/083692

PCT Pub. Date: Oct. 24, 2002

(65) Prior Publication Data

US 2004/0132992 A1    Jul. 8, 2004

(30) Foreign Application Priority Data

Apr. 18, 2001   (KR) .............................. 2001-20673

(51) Int. Cl.
*C07D 501/22*   (2006.01)
(52) U.S. Cl. ....................... 540/215; 540/222
(58) Field of Classification Search ............... 540/222, 540/215
See application file for complete search history.

(56) References Cited

U.S. PATENT DOCUMENTS

| | | | | |
|---|---|---|---|---|
| 4,694,079 A | * | 9/1987 | Crast, Jr. | 540/215 |
| 4,699,979 A | * | 10/1987 | Hoshi et al. | 540/215 |
| 4,708,955 A | * | 11/1987 | Iimura et al. | 514/202 |
| 6,903,211 B1 | * | 6/2005 | Deshpande et al. | 540/215 |

* cited by examiner

*Primary Examiner*—Mark L. Berch
(74) *Attorney, Agent, or Firm*—Anderson Kill & Olick, PC

(57) ABSTRACT

A 3-(Z)-propenyl cephem compound is selectively prepared by reacting a phosphoranylidene cephem compound with acetaldehyde in the presence of a base in a solvent mixture comprising diethyl ether, formula (I), wherein R is a carboxyl protecting group; $R^1$ is hydrogen or $R^2CH_2CO$—; and $R^2$ is ethyl, 2-thiophenyl, phenyl, p-hydroxyphenyl or phenoxy

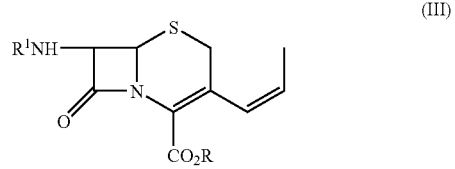

(III)

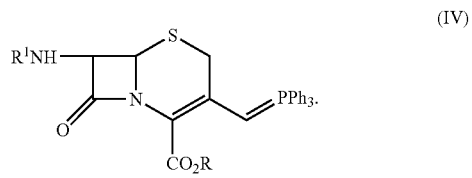

(IV)

15 Claims, No Drawings

PROCESS FOR THE SELECTIVE PREPARATION OF 3-(Z) PROPENYL-CEPHEM COMPOUND

FIELD OF THE INVENTION

The present invention relates to a process for selectively preparing 3-(Z)-propenyl cephem, an intermediate for use in the preparation of cefprozil.

BACKGROUND OF THE INVENTION

Cefprozil, an oral cephalosporin antibiotic, is a mixture of antibiotic BMY-28100 of formula I (the Z- or cis-isomer) and antibiotic BMY-28167 of formula II (the E- or trans-isomer), the mixture having a Z- to E-isomer ratio in the range of 89:11 to 94:6. The preparation of cefprozil is usually carried out using a 3-(Z)-propenyl cephem of formula III.

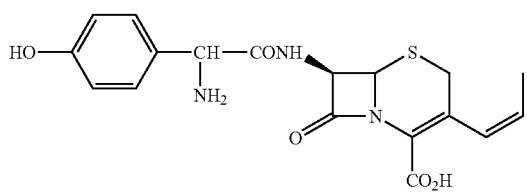

(I)

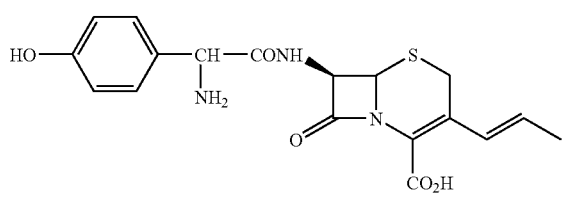

(II)

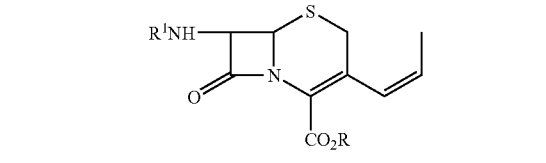

(III)

wherein R is a carboxyl protecting group; $R^1$ is hydrogen or $R^2CH_2CO-$; and $R^2$ is ethyl, 2-thiophenyl, phenyl, p-hydroxy or phenoxy.

The propenyl group at position $C_3$ of the cephem compound is usually introduced by the so-called Wittig reaction which produces both Z- and E-isomers of the propenyl double bond. As cefprozil has a Z-isomer content in the range of 89 to 94%, there have been reported many methods for adjusting the Z- to E-isomer ratio, e.g., in the Wittig reaction product.

For example, U.S. Pat. No. 4,699,979 discloses a method of raising the Z- to E-isomer ratio to about 9:1 by conducting a Wittig reaction in the presence of about 10 equivalents of LiBr based on the phosphoranylidene cephem compound with benzylidene amino protection group. However, this method is not applicable to other compounds having an amino protective group other than benzylidene.

U.S. Pat. No. 4,727,070 teaches a method of converting a cefprozil composition containing 85% Z-isomer and 15% E-isomer into an imidazolidinone sodium derivative, removing E-imidazolidinone sodium by a different solubility, and then treating with 1N HCl, to obtain cefprozil containing 98.5% Z-isomer and 1.5% E-isomer. Although the product purity is good, this two-step purification method gives a low yield of about 78%.

International Patent Application No. PCT/EP 92/02965 also discloses a method of lowering the E-isomer content by exploiting solubility differences of various salts of the E- and Z-isomers of deprotected cephem. This method also has disadvantages of a low efficiency and low yield.

SUMMARY OF THE INVENTION

It is, therefore, an object of the present invention to provide an improved method for preparing a 3-(Z)-propenyl cephem derivative with a high selectivity and yield.

In accordance with the present invention, there is provided a process for selectively preparing a 3-(Z)-propenyl cephem compound of formula III which comprises reacting a phosphoranylidene cephem compound of formula IV with acetaldehyde in the presence of a base in a solvent mixture comprising diethyl ether:

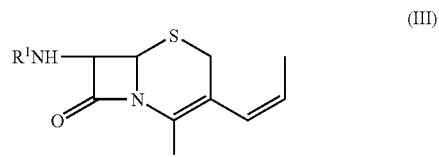

(III)

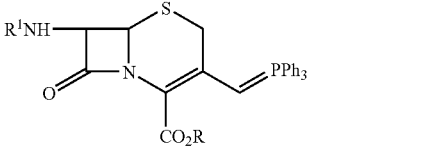

(IV)

wherein R is a carboxyl protecting group; $R^1$ is hydrogen or $R^2CH_2CO-$; and $R^2$ is ethyl, 2-thiophenyl, phenyl, p-hydroxyphenyl or phenoxy.

DETAILED DESCRIPTION OF THE INVENTION

A phosphoranylidene cephem compound of formula IV may be prepared by treating a phosphonium derivative obtained by reacting a 3-halomethyl cephem compound of formula V (A product named GCLE, wherein R is p-methoxybenzyl, $R^2$ is phenyl and X is Cl, is commercially available) with triphenylphosphine, in the presence of a base such as sodium carbonate and sodium hydroxide:

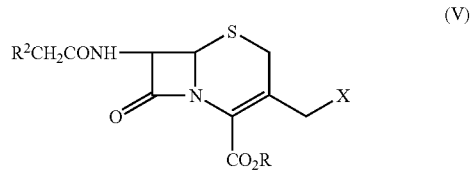

(V)

wherein R is a carboxyl protecting group; $R^2$ is ethyl, 2-thiophenyl, phenyl, p-hydroxyphenyl or phenoxy; and X is Cl, Br or I.

The carboxyl protecting group in the compound of formula III may be any of the conventional protecting group used in phsphosporin derivatives, e.g., t-butyl, allyl, benzyl, p-methoxybenzyl, p-nitrobenzyl, triphenylmethyl and diphenylmethyl.

The 3-(Z)-propenyl cephem compound employed in the present invention is prepared by reacting a phosphoranylidene cephem compound of formula IV with acetaldehyde in the presence of a base in a two-phase solvent system, the organic phase thereof essentially comprising a diethyl ether. When such a Wittig reaction is conducted using a conventional organic solvent such as methylene chloride and tetrahydrofuran, it is difficult to raise the Z-isomer content to above 83% regardless of how the reaction conditions are varied. In contrast, it is possible to obtain a product having a Z-isomer content of more than 90% when the Wittig reaction is carried out in a solvent system comprising diethyl ether in accordance with the present invention.

Since diethyl ether does not readily dissolve a phosphoranylidene cephem compound of formula IV, the organic solvent phase employed in the present invention further comprises a second organic solvent which may be acetonitrile, tetrahydrofuran, 1,4-dioxane, ethyl acetate or methyl acetate, preferably tetrahydrofuran. The second organic solvent is preferably used in an amount of ⅓ to 2 based on the volume of diethyl ether. The total volume of the organic solvent mixture employed in the present invention is in the range from 5 to 30, preferably 10 to 20 ml per gram of the phosphoranylidene cephem compound of formula IV used.

The amount of acetaldehyde used in the present invention is 10 to 50 equivalents, preferably 15 to 30 equivalents based on the amount of the phosphoranylidene cephem compound.

When a Wittig reaction is performed in the absence of an added base, the yield is low such as from 40 to 60%. However, the addition of a base enhances the yield to about 90% without reducing the Z-isomer selectivity. The base used in the present invention is an organic base such as triethylamine, N-methylmorpholine, pyrrolidine, piperidine, benzylamine, diethylamine, diisopropylethylamine, dimethylethylamine, dimethylbenzylamine, triethanolamine, tetramethylethylenediamine and dimethylethylidenediamine and an inorganic base such as sodium carbonate, sodium hydroxide, lithium hydroxide, and potassium hydroxide. Triethylamine and sodium hydroxide are preferred.

The amount of the base employed in the present invention is preferably 0.1 to 1.0 equivalent, more preferably 0.2 to 0.4 equivalent based on the amount of phosphoranylidene cephem compound of formula IV in case an organic base or sodium carbonate is employed, while 0.01 to 0.1 equivalent, preferably 0.02 to 0.05 equivalent, in case sodium hydroxide, lithium hydroxide or potassium hydroxide is used.

The Wittig reaction in accordance with the present invention may be performed at a temperature ranging from 5 to 40° C., preferably from 10 to 30° C., for a period sufficient to complete the reaction, e.g., about 8 to 20 hours.

The method of the present invention is very simple, and gives a high yield (80% or higher) of 90 to 94% pure 3-(Z)-propenyl cephem compound.

The following Examples are intended to further illustrate the present invention only, and are not intended to limit the scope of the invention.

PREPARATION EXAMPLE

Preparation of p-methoxybenzyl 8-oxo-7-phenylacetamino-3[(triphenyl-15-phosphoranylidene)-methyl-5-thia-1-aza-bicyclo[4.2.0]oct-2-en-2-carboxylate (Phosphoranylidene as a Starting Material)

100 g (0.205 mol) of p-methoxybenzyl 3-chloromethyl-7-phenylacetamido-3-cephem-4-carboxylate (3-chloromethyl cephem compound: GCLE), 32.3 g (0.216 mol) of sodium iodide and 59.1 g (0.226 mmol) of triphenylphosphine were mixed with 100 ml of methylene chloride, 200 ml of hydrofuran and 50 ml of water were added thereto and stirred at 30 to 35° C. for 1 hour. Then, the reaction mixture was cooled to room temperature, 500 ml of 10% sodium thiosulfate was added thereto, and stirred for 30 minutes. The aqueous layer was removed, and a NaOH solution (9 g of sodium hydroxide in 500 ml of water) was added to the organic layer. The mixture was vigorously stirred at room temperature for 1 hour, the aqueous layer was removed, 500 ml of 10% aqueous sodium thiosulfate was added to the organic layer, and stirred for 30 minutes. After removing the aqueous layer, the organic layer was dried over anhydrous magnesium sulfate and the solvent was distilled off to obtain a brown residual syrup. 500 ml of acetone was added to the residue, stirred for 30 minutes, and cooled to about 0° C. The solid formed was filtered, washed with acetone, and then dried in a vacuum to obtain 124 g of the title compound as a yellow solid (Yield: 85%).

H-NMR (δ, CDCl$_3$): 2.44, 2.66(2 h, ABq, C-2), 3.59(2H, s, PhCH$_2$), 3.85(3H, s, —OCH$_3$), 5.06~5.24(3H, m, CO$_2$=CH$_2$, C-6), 5.52(1H, d, C-7), 6.83(1H, d, benzene-H), 7.12~7.65(23H, m, —CH=CPPh$_3$, benzene-H)

EXAMPLE 1

Preparation of p-methoxybenzyl 7-phenylacetamido-3-[propen-1-yl]-3-cephem-4-carboxylate (Z-rich propenyl cephem)

200 g of sodium chloride, 1 L of water, 1 L of diethyl ether, 500 ml of tetrahydrofuran and 28 ml of 0.1N sodium hydroxide were mixed and cooled to 10° C. 100 g of the phosphoranylidene compound prepared in the Preparation Example was added thereto, followed by adding 140 ml of acetaldehyde dropwise thereto. The reaction mixture was stirred for 20 hours while maintaining the temperature at 10 to 15° C. 10 ml of concentrated hydrochloric acid was added to the reaction mixture and stirred for 10 minutes. Then, the organic layer was separated, dried over anhydrous magnesium sulfate, filtered and distilled to remove the solvent. 150 ml of isopropanol was added to the residue formed, refluxed, cooled to about 0° C. The precipitated solid was filtered, washed with isopropanol, and then dried in a vacuum to give 57.8 g of the title compound as a light yellow solid. (Yield: 86% and Content of Z-isomer: 91.5%, Z-isomer:E-isomer=10.8:1.0)

H-NMR (δ, DMSO-d$_6$): 1.52(3H×10.8/11.8, d, (Z)-CH$_3$), 1.73(3H×1.0/11.8, d, (E)-CH$_3$), 3.36~3.68(4H, m, PhCH$_2$, C-2), 3.75(3H, s, —OCH$_3$), 5.06~5.24(3H, m, CO$_2$=CH$_2$, C-6), 5.52~5.69(2H, d, —CH=CH(CH$_3$), C-7), 6.06(1H, d, —CH=CH(CH$_3$)), 6.91(2H, d, benzene-H), 7.19~7.62(7H, m, benzene-H)

COMPARATIVE EXAMPLE

Preparation of p-methoxybenzyl 7-phenylacetamido-3-[propen-1-yl]-3-cephem-4-carboxylate (Preparation of Z-propenyl cephem without using ether)

The procedure of Example 1 was repeated except for using 1500 ml of tetrahydrofuran in place of 1 L of diethyl ether and 500 ml of tetrahydrofuran, to obtain the title compound. (Yield: 54% and Content of Z-isomer: 82.1%, Z-isomer:E-isomer=4.6:1.0).

H-NMR (δ, DMSO-$d_6$): 1.53(3H×4.6/5.6, d, (Z)-$CH_3$), 1.75(3H×1.0/5.6, d, (E)-$CH_3$), 3.34~3.67(4H, m, Ph<u>CH</u>$_2$, C-2), 3.73(3H, s, —$OCH_3$), 5.04~5.21(3H, m, $CO_2$=<u>CH</u>$_2$, C-6), 5.51~5.67(2H, d, —<u>CH</u>=CH($CH_3$), C-7), 6.04(1H, d, —CH=<u>CH</u>($CH_3$)), 6.87(2H, d, benzene-H), 7.20~7.63(7H, m, benzene-H)

EXAMPLE 2

Preparation of p-methoxybenzyl 7-amino-3-[propen-1-yl]-3-cephem-4-carboxylate.HCl 32.6 g (0.157 mol) of phosphorous pentachloride was suspended in 250 ml of methylene chloride, cooled to −20° C., 11.7 ml (0.146 mol) of pyridine was added dropwise thereto while maintaining the temperature at below −10° C., and stirred for 30 minutes. 50 g (0.104 mol) of the Z-rich propenyl cephem compound prepared in Example 1 was added thereto, followed by stirring at 0 to −5° C. for 2 hours. The reaction mixture was cooled to −20° C., 68 ml of 1,3-butanediol was added dropwise thereto, and stirred at room temperature for 1.5 hours. The reaction mixture was washed with 250 ml of water, and the organic layer was separated, dried over anhydrous magnesium sulfate, filtered and distilled to remove the solvent. 250 ml of ethyl acetate was added to the dark red oily residue obtained, stirred for 1 hour and then 250 ml of diethyl ether was added dropwise thereto to stir for 30 minutes. Then the precipitated solid was filtered, washed with ether and dried in a vacuum to obtain 36.3 g of the title compound as light yellow solid (Yield: 88% and Content of Z-isomer: 91.9%, Z-isomer:E-isomer=11.3:1.0).

H-NMR (δ, DMSO-$d_6$): 1.53(3H×11.3/12.3, d, (Z)-$CH_3$), 1.82(3H×1.0/12.3, d, (E)-$CH_3$), 3.65(2H, q, C-2), 3.73(3H, s, —$OCH_3$), 5.06~5.27(3H, m, $CO_2$=<u>CH</u>$_2$,C-6), 5.64~5.75 (1H, m, —<u>CH</u>=CH($CH_3$), C-7), 6.18(1H, d, —CH=<u>CH</u>($CH_3$)), 6.94(2H, d, benzene-H), 7.32(2H, d, benzene-H)

While the invention has been described with respect to the above specific embodiments, it should be recognized that various modifications and changes may be made to the invention by those skilled in the art which also fall within the scope of the invention as defined by the appended claims.

What is claimed is:

1. A process for preparing a 3-(Z)-propenyl cephem compound of formula III which comprises reacting a phosphoranylidene cephem compound of formula IV with acetaldehyde in the presence of a base in a solvent mixture comprising diethyl ether:

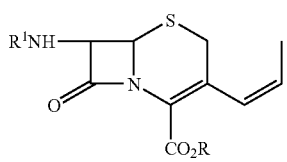

(III)

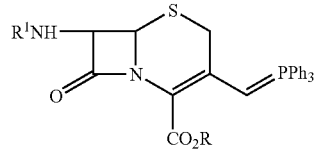

(IV)

wherein R is a carboxyl protecting group; $R^1$ is hydrogen or $R^2CH_2CO$—; and $R^2$ is ethyl, 2-thiophenyl, phenyl, p-hydroxyphenyl or phenoxy.

2. The process of claim 1, wherein the solvent mixture further comprises an organic solvent selected from the group consisting of acetonitrile, tetrahydrofuran, 1,4-dioxane, ethyl acetate and methyl acetate.

3. The process of claim 2, wherein the organic solvent is tetrahydrofuran.

4. The process of claim 1, wherein the total volume of the solvent mixture is in the range of 5 to 30 ml per gram of the phosphoranylidene cephem compound of formula IV.

5. The process of claim 4, wherein the total volume of the solvent mixture is in the range of 10 to 20 ml per gram of the phosphoranylidene cephem compound of formula IV.

6. The process of claim 1, wherein the base is an organic base selected from the group consisting of triethylamine, N-methylmorpholine, pyrrolidine, piperidine, benzylamine, diethylamine, diisopropylethylamine, dimethylethylamine, dimethylbenzylamine, triethanolamine, tetramethylethylenediamine, and dimethylethylidenediamine, or an inorganic base selected from the group consisting of sodium carbonate, sodium hydroxide, lithium hydroxide and potassium hydroxide.

7. The process of claim 6, wherein the base is triethylamine or sodium hydroxide.

8. The process of claim 6, wherein the base is an organic base or sodium carbonate, and is employed in an amount ranging from 0.1 to 1.0 equivalent based on the amount of the phosphoranylidene cephem compound of formula IV.

9. The process of claim 6, wherein the base is sodium hydroxide, lithium hydroxide or potassium hydroxide, and is employed in an amount ranging from 0.01 to 0.1 equivalent based on the amount of the phosphoranylidene cephem compound of formula IV.

10. The process of claim 2, wherein a volume of the organic solvent is in the range of ⅓ to 2 based on the volume of the diethyl ether.

11. The process of claim 3, wherein a volume of the organic solvent is in the range of ⅓ to 2 based on the volume of the diethyl ether.

12. The process of claim 2, wherein the total volume of the solvent mixture is in the range of 5 to 30 ml per gram of the phosphoranylidene cephem compound of formula IV.

13. The process of claim 3, wherein the total volume of the solvent mixture is in the range of 5 to 30 ml per gram of the phosphoranylidene cephem compound of formula IV.

14. The process of claim 12, wherein the total volume of the solvent mixture is in the range of 10 to 20 ml per gram of the phosphoranylidene cephem compound of formula IV.

15. The process of claim 13, wherein the total volume of the solvent mixture is in the range of 10 to 20 ml per gram of the phosphoranylidene cephem compound of formula IV.

* * * * *